United States Patent
Kollgaard et al.

(10) Patent No.: US 7,895,895 B2
(45) Date of Patent: Mar. 1, 2011

(54) METHOD AND APPARATUS FOR QUANTIFYING POROSITY IN A COMPONENT

(75) Inventors: Jeffrey R. Kollgaard, Kent, WA (US); Carrie Ann Decker, Seattle, WA (US); Barry A. Fetzer, Renton, WA (US); Kevin M. Uhl, Snohomish, WA (US)

(73) Assignee: The Boeing Company, Chicago, IL (US)

( * ) Notice: Subject to any disclaimer, the term of this patent is extended or adjusted under 35 U.S.C. 154(b) by 662 days.

(21) Appl. No.: 11/781,614

(22) Filed: Jul. 23, 2007

(65) Prior Publication Data

US 2009/0025479 A1 Jan. 29, 2009

(51) Int. Cl.
*G01N 29/11* (2006.01)
*G01N 29/42* (2006.01)

(52) U.S. Cl. .................... 73/599; 73/602; 73/609
(58) Field of Classification Search .............. 73/599, 73/600, 602, 609, 614
See application file for complete search history.

(56) References Cited

U.S. PATENT DOCUMENTS 7,010,980 B2 * 3/2006 Meier .......................... 73/602
7,353,709 B2 * 4/2008 Kruger et al. .................. 73/599
2007/0095141 A1 5/2007 Puckett
2007/0101815 A1 5/2007 Kollgaard et al.
2008/0148854 A1 6/2008 Georgeson et al.

OTHER PUBLICATIONS

Hagemaier, D. et al., "Nondestructive Testing of Graphite Fiber Composite Structures", Society of Automotive Engineers, No. 700750, National Aeronautice and Space Engineering and Manufacturing Meeting, Los Angeles, Calif. Oct. 5-9, 1970, pp. 1-11.*
Mitri, F.G. et al., "Surface Roughness Imaging Using the Acosutic Emission Induced by the Dynamic Radiation Force of Ultrasound", Applied Physics Letters, vol. 88, 2006, pp. 234105-1 through 234105-3.*

* cited by examiner

*Primary Examiner* — Daniel S Larkin
(74) *Attorney, Agent, or Firm* — Yee & Associates, P.C.; Dennis R. Plank (57) ABSTRACT

A computer implemented method, or hardware filtration apparatus, and computer usable program code for measuring porosity in materials. An ultrasonic signal is emitted from a transmitting transducer in an ultrasonic measurement system into a material. A response signal is received at a receiving transducer in the ultrasonic measurement system from the material. The response signal is filtered to pass only frequencies in the response signal within a selected frequency range to form a filtered response signal. A porosity level of the material is identified using the filtered response signal.

17 Claims, 9 Drawing Sheets

METHOD AND APPARATUS FOR QUANTIFYING POROSITY IN A COMPONENT

BACKGROUND INFORMATION

1. Field

The present disclosure relates generally to the production of components and in particular to the quantification of porosity in components. Still more particularly, the present disclosure relates to a method and apparatus for measuring the porosity of materials using ultrasonic measurement methods.

2. Background

Aircraft are being designed and manufactured with greater percentages of composite materials. Some aircraft may have more than fifty percent of their primary structure made from composite materials. Composite materials are being used in aircraft to decrease the weight of the aircraft. This decreased weight improves payload capacities and fuel efficiencies. Further, composite materials also may provide improved corrosion and fatigue resistance for various components in an aircraft.

Composite materials are tough, light-weight materials created by combining two or more dissimilar components to create a component with stronger properties than the original materials. Composite materials are typically non-metal materials. For example, a composite may include fibers and resins. The fibers and resins may be combined by curing or heating these components to form a cured product for the composite material.

In particular, key components, such as wings and fuselage skins, are now being constructed exclusively with composite materials, such as a composite laminate. With more and more critical structures being made of composite laminates, methods and techniques to assure that these components meet quality standards are needed more than ever before.

Porosity is a known undesirable condition that may occur during processing to create composite components. Porosity occurs when voids are present in a material caused by evolved gases. Currently, much time, effort, and money is spent on ultrasonic measurement systems that are designed to detect and quantify the porosity in composite components, such as those made using carbon laminates. These currently used techniques take advantage of the fact that porosity does not block ultrasound signals but attenuates these signals. By measuring the amount of attenuation that occurs when transmitting an ultrasonic signal into a composite component, an estimate of the degree of porosity may be obtained for correlation with manufacturing specifications.

The estimate of the degree or level of porosity for a particular material may be determined with an attenuation curve. A porosity attenuation curve is generated using samples with known amounts of porosity. With an increasing amount of porosity, the ultrasonic signal has an increasing level of attenuation. This curve may have an acceptable variance or tolerance level to indicate acceptable measurements that indicate a certain level of porosity.

In practice, however, some difficulties exist with this approach. Attenuation curves are produced to represent porosity attenuation for a specific type of material that is to be tested. The actual porosity levels measured, however, are also specific to a particular ultrasonic measurement system and not just to the material. As a result, different ultrasonic systems or instrument configurations at different component production locations may produce widely different results. This variance in results may occur because of differences between the different ultrasonic measurement systems. A primary factor that may cause different results is the varied frequency spectra of the transducers or the ultrasonic system receiver electronics.

As a result, having a universally applicable attenuation curve is not possible, as the equipment characteristics at different sites may be different. This would result in a part passing the specification tolerance at one site but failing the specification tolerance at another site. To mitigate or reduce the problem of varying results, an approach is used in which sets of porosity reference calibration standards are manufactured for each site at which testing occurs. These calibration standards are used instead of attenuation curves. These sets of porosity reference calibration standards are samples of materials with known porosities.

Currently, these standards are made of graphite epoxy with cure parameters altered to produce varying degrees of porosity. The porosity of these samples is determined by a cross-sectional area porosity content analysis and can be correlated with the attenuation value. This approach of creating multiple calibration standards is a time consuming and expensive process. Full sets of these component calibrations are manufactured and provided to each site or supplier who produces parts that require assessment of porosity levels. The set of calibration standards are then used with an ultrasonic measurement system at a particular site. Care must be taken to ensure that all of the replicate sets used at different locations are equal in terms of ultrasonic response.

When testing a composite part, the ultrasonic measurement system is first calibrated using the calibration standards. These standards are tested and interrogated to identify a result that is generated for each known level of porosity. Then, the particular part may be tested and the results from that test are compared to the results generated from interrogating or testing the calibration standards.

With the increased use of composites in aircraft, the number of sites or suppliers performing porosity evaluation increases. This increase causes a need for more calibration standards, requiring an increase in time and effort needed to generate these calibration standards for each site or supplier. Furthermore, the increased use of composite materials on an aircraft has created a need to quantify porosity in aircraft maintenance operations, such as in the case of post-repair inspection of bonded repairs. As a result, the expense and effort needed to produce and maintain aircraft increases with the current testing systems used for porosity.

SUMMARY

The advantageous embodiments provide a computer implemented method and apparatus for measuring porosity in materials. An ultrasonic signal is emitted from a transmitting transducer in an ultrasound testing system into a material. A response signal is received at a receiving transducer in the ultrasonic measurement system from the material. The response signal is filtered to pass only frequencies in the response signal within a selected frequency range to form a filtered response signal. A porosity level of the material is identified using the filtered response signal.

In another advantageous embodiment, a method is used for measuring porosity in materials wherein a signal is transmitted into a material. A response from the signal is received and filtered to pass only a selected range of frequencies to form a filtered signal. The filtered signal is compared to a reference signal to identify a porosity level of the material.

In yet another advantageous embodiment, an apparatus is capable of generating an ultrasound signal. The apparatus comprises an ultrasound signal generation unit that has a transmitting transducer, a receiving transducer, a filter, and an ultrasound receiver. The transmitting transducer is connected to the ultrasound signal generation unit, wherein the transmitting transducer is capable of transmitting the ultrasound signal into a material. The receiving transducer is capable of receiving a response signal generated by the transmitting transducer transmitting the ultrasound signal into the material. The filter is capable of filtering the response signal received by the receiving transducer to form a modified response that includes only frequencies within a selected range. The ultrasound receiver is connected to the receiving transducer, wherein the ultrasound receiver is capable of presenting the modified response.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
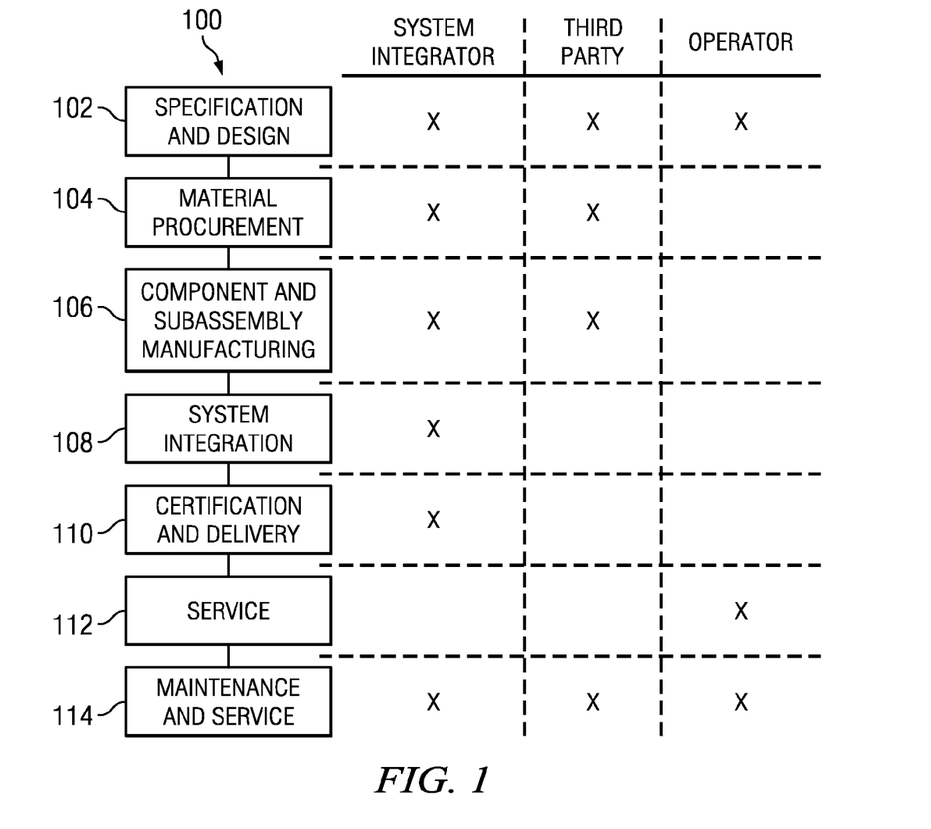
FIG. 1 is a flow diagram of an aircraft manufacturing and service method in which an advantageous embodiment may be implemented.
Figure 2:
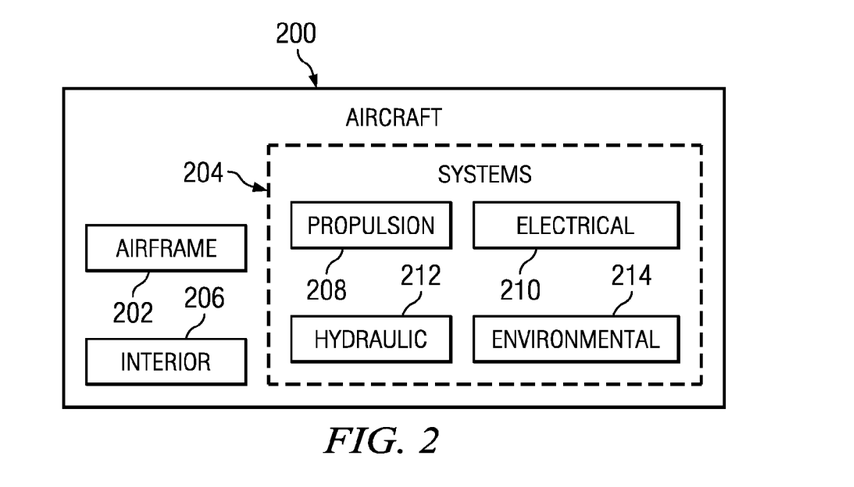
FIG. 2 is a diagram of an aircraft containing components that may be tested using an advantageous embodiment.

Referring more particularly to the drawings, embodiments of the disclosure may be described in the context of aircraft manufacturing and service method 100 as shown in FIG. 1 and aircraft 200 as shown in FIG. 2. During pre-production, aircraft manufacturing and service method 100 in FIG. 1 may include specification and design 102 of aircraft 200 in FIG. 2 and material procurement 104. During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator as indicated by the "X" in the grid to the right of the flow diagram of FIG. 1. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

As shown in FIG. 2, aircraft 200, produced by aircraft manufacturing and service method 100 in FIG. 1, may include airframe 202 with systems 204 and interior 206. Examples of systems 204 include one or more of propulsion system 208, electrical system 210, hydraulic system 212, and environmental system 214.

Apparatus and methods embodied herein may be employed during any one or more of the stages of production and aircraft manufacturing and service method 100 in FIG. 1. For example, components or subassemblies provided in component and subassembly manufacturing 106 may be fabricated or manufactured in a manner similar to components or subassemblies produced or repaired while aircraft 200 is in service.

Also, one or more apparatus embodiments, method embodiments, or a combination thereof may be utilized during production stages for component and subassembly manufacturing 106 and system integration 108 in FIG. 1, for example, by reducing the weight of aircraft 200. For example, the composite fastener system in the advantageous embodiments may be used in assembling structural and other composite components in aircraft 200. The use of these composite fastening systems reduces the weight of aircraft 200. These additional weight savings may aid in increasing fuel savings and increasing payload capacity for aircraft 200.

The different advantageous embodiments provide a method for measuring porosity in materials. A signal is transmitted into a material and a response to the signal is received. The response is filtered to pass only a selected range of frequencies. The filtered response is then used to identify the porosity level of the material.

The different illustrative embodiments enable use of a universal attenuation curve. An attenuation curve is a curve with a set of data points that identify porosity levels for particular responses returned from transmitting a signal into a material. In these examples, the signal is an ultrasound signal. An ultrasound signal is a cyclic sound pressure with a frequency greater than an upper limit of human hearing, such as 20 KHz.

The different advantageous embodiments provide an identification of a filter for use in processing response signals. The filter provides an ability to use the same universal attenuation curve on different ultrasonic measurement systems that may have variations between each other. Those variants include, for example, differences in the frequency sensitivity spectra in the transducers, the frequency content of pulses, and the frequency bandwidth of the receiver. The different advantageous embodiments eliminate the need to provide porosity calibration standards in the form of panels or sample materials to different suppliers, locations, or groups that may perform porosity tests.

Figure 3:
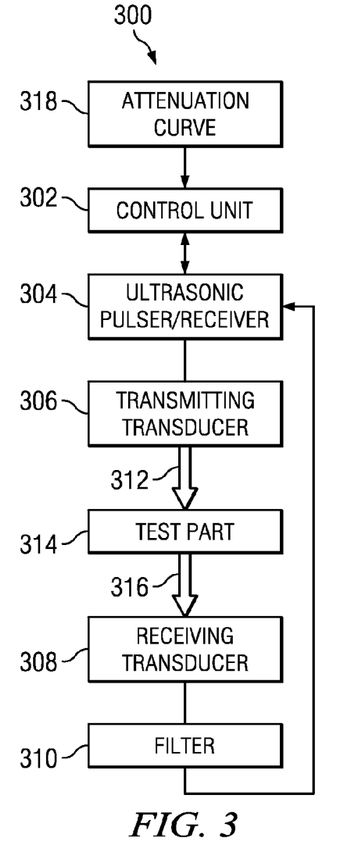
FIG. 3 is a diagram of an ultrasonic measurement system in accordance with an advantageous embodiment.

Turning now to FIG. 3, a diagram of an ultrasonic measurement system is depicted in accordance with an advantageous embodiment. Ultrasonic measurement system 300 is used to measure changes in ultrasonic signals transmitted into a material. In particular, ultrasonic measurement system 300 may be used to determine porosity levels in a material by measuring the attenuation of signals transmitted through the material. In this example, ultrasonic measurement system 300 is a through-transmission system.

Ultrasonic measurement system 300 includes control unit 302, ultrasonic pulser/receiver 304, transmitting transducer 306, receiving transducer 308, and filter 310. Ultrasonic pulser/receiver 304 generates signals of varying frequencies that are transmitted by transmitting transducer 306 as signal 312. These signals pass through test part 314 to form response signal 316, which is received by receiving transducer 308. Signal 312 may be attenuated while passing through test part 314 to form response signal 316. Attenuation is caused by voids present in test part 314. Response signal 316 is filtered by filter 310 with the filtered signal then being sent to ultrasonic pulser/receiver 304. This filtered signal may then be sent to control unit 302 for processing.

Control unit 302 may display the signal as received or may provide an indication of the porosity level of the section of test part 314 being tested. Further, control unit 302 may compare the porosity levels with requirements for different parts to determine whether test part 314 passes inspection.

In these examples, the filtered result is compared with attenuation curve 318 to identify the porosity level. Attenuation curve 318 provides a standard by which the filtered data may be compared in identifying porosity levels of test part 314. A different attenuation curve may be provided for each type of material that is being tested. Different types of composite components may have different attenuation curves for the desired porosity level.

In these examples, filter 310 filters response signal 316 to only pass frequencies within a selected range of frequencies within response signal 316. In particular, in these examples, filter 310 takes the form of a bandpass filter. Of course, any other type of filter may be used, depending on the particular implementation and desired frequencies. Filter 310 is illustrated as being connected "downstream" of receiving transducer 308, in these examples. Depending on the particular implementation, filter 310 also could be connected to the output of transmitting transducer 306 to emit in the desired range. Further, filter 310 may be implemented as a software filter within control unit 302, depending on the particular implementation.

Figure 4:
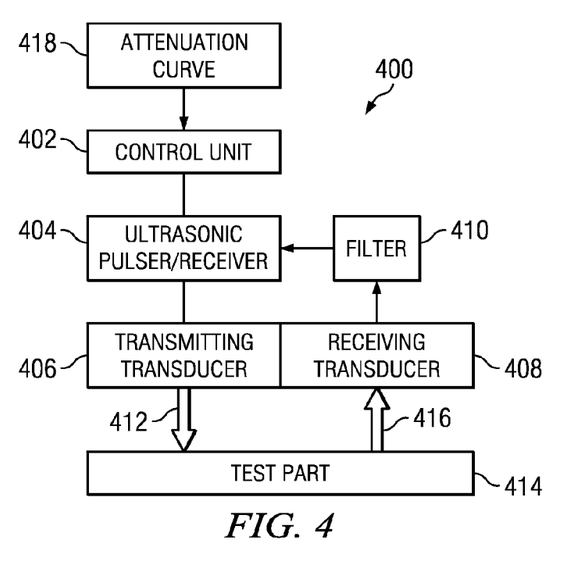
FIG. 4 is a diagram of another configuration for an ultrasonic measurement system in accordance with an advantageous embodiment.

Turning now to FIG. 4, a diagram of another configuration for an ultrasonic measurement system is depicted in accordance with an advantageous embodiment. In this example, ultrasonic measurement system 400 is a "pitch-catch" (two transducer) pulse-echo system. Ultrasonic measurement system 400, in this example, includes control unit 402, ultrasonic pulser/receiver 404, transmitting transducer 406, receiving transducer 408, and filter 410. In this particular example, transmitting transducer 406 transmits signal 412 into test part 414. A portion of signal 412 is reflected and received by receiving transducer 408 as response signal 416. In a similar fashion, as with ultrasonic measurement system 300 in FIG. 3, response signal 416 is filtered using filter 410 to provide a filtered signal for analysis by control unit 402 using attenuation curve 418.

Figure 5:
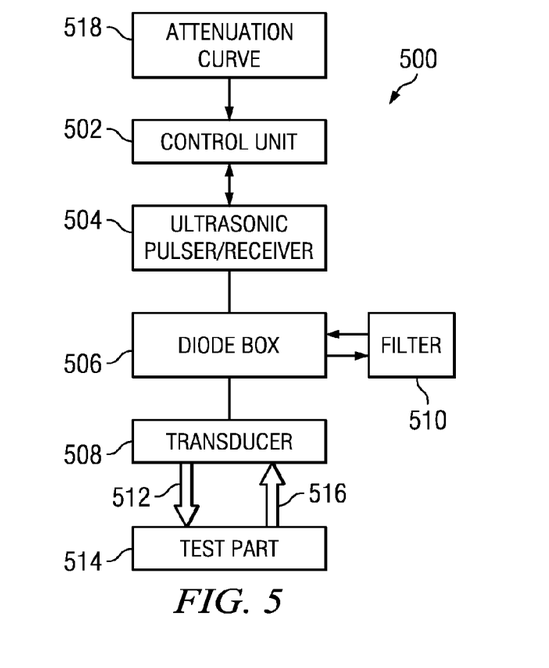
FIG. 5 is a diagram of yet another configuration for an ultrasonic measurement system in accordance with an advantageous embodiment.

With reference next to FIG. 5, a diagram of yet another configuration for an ultrasonic measurements system is depicted in accordance with an advantageous embodiment. In this example, ultrasonic measurement system 500 represents a single transducer pulse echo measurement system. Ultrasonic measurement system 500, in this example, includes control unit 502, ultrasonic pulser/receiver 504, diode box 506, transducer 508, and filter 510.

In this illustrative example, transducer 508 functions both as a transmitting transducer and a receiving transducer. In a transmitting mode, transducer 508 transmits signal 512 into test part 514. Transducer 508 also functions to detect or receive response signal 516.

Diode box 506 steers response signal 516 through filter 510 and receives a filtered signal that is then sent to ultrasonic pulser/receiver 504. Various other types of components may be used in place of diode box 506, depending on the particular implementation. Other types of components may be selected that may switch the path of response signal 516 through filter 510. This filtered signal may then be analyzed by control unit 502 through comparison to the attenuation curve 518.

The illustration of ultrasonic measurement system 300 in FIG. 3, ultrasonic measurement system 400 in FIG. 4, and ultrasonic measurement system 500 in FIG. 5 are presented for purposes of illustration and not meant to provide architectural implementations in the manner in which the different advantageous embodiments may be implemented in an ultrasonic measurement system.

Figure 6:
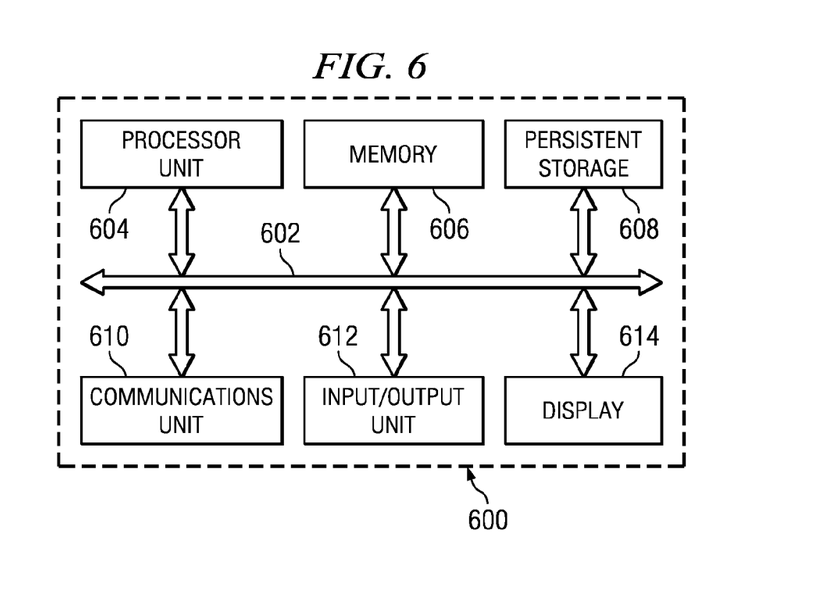
FIG. 6 is a diagram of a data processing system in accordance with an advantageous embodiment.

Turning now to FIG. 6, a diagram of a data processing system is depicted in accordance with an advantageous embodiment. Data processing system 600 is an example of a device that may be used to implement an ultrasonic testing system. In this illustrative example, data processing system 600 includes communications fabric 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multiprocessor core, depending on the particular implementation. Further, processor unit 604 may be implemented using one or more heterogeneous processor systems in which a main processor is present with secondary processors on a single chip. As another illustrative example, processor unit 604 may be a symmetric multiprocessor system containing multiple processors of the same type.

Memory 606, in these examples, may be, for example, a random access memory. Persistent storage 608 may take various forms depending on the particular implementation. For example, persistent storage 608 may contain one or more components or devices. For example, persistent storage 608 may be a hard drive, a flash memory, a rewritable optical disk, a rewritable magnetic tape, or some combination of the above. The media used by persistent storage 608 also may be removable. For example, a removable hard drive may be used for persistent storage 608.

Communications unit 610, in these examples, provides for communications with other data processing systems or devices. In these examples, communications unit 610 is a network interface card. Communications unit 610 may provide communications through the use of either or both physical and wireless communications links. Results of testing composite materials may be transmitted to a remote database through communications unit 610. Also, attenuation curves and identifications of filters for use in testing components may be received through communications unit 610.

Input/output unit 612 allows for input and output of data with other devices that may be connected to data processing system 600. In these examples, input/output unit 612 provides a connection to an ultrasonic pulser/receiver unit. The connection provides a communications link used to send commands to the ultrasonic pulser/receiver unit and to receive response signals for analysis. As another example, input/output unit 612 may provide a connection for user input through a keyboard and mouse. Further, input/output unit 612 may send output to a printer. Display 614 provides a mechanism to display information to a user.

Instructions for the operating system and applications or programs are located on persistent storage 608. These instructions may be loaded into memory 606 for execution by processor unit 604. The processes of the different embodiments may be performed by processor unit 604 using computer implemented instructions, which may be located in a memory, such as memory 606. These instructions are referred to as computer usable program code or computer readable program code that may be read and executed by a processor in processor unit 604. The computer readable program code may be embodied on different physical or tangible computer readable media, such as memory 606 or persistent storage 608.

The different components illustrated for data processing system 600 are not meant to provide architectural limitations to the manner in which different embodiments may be implemented. The different illustrative embodiments may be implemented in a data processing system including components in addition to or in place of those illustrated for data processing system 600. Other components shown in FIG. 6 can be varied from the illustrative examples shown.

For example, a bus system may be used to implement communications fabric 602 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 606 or a cache such as found in an interface and memory controller hub that may be present in communications fabric 602.

Figure 7:
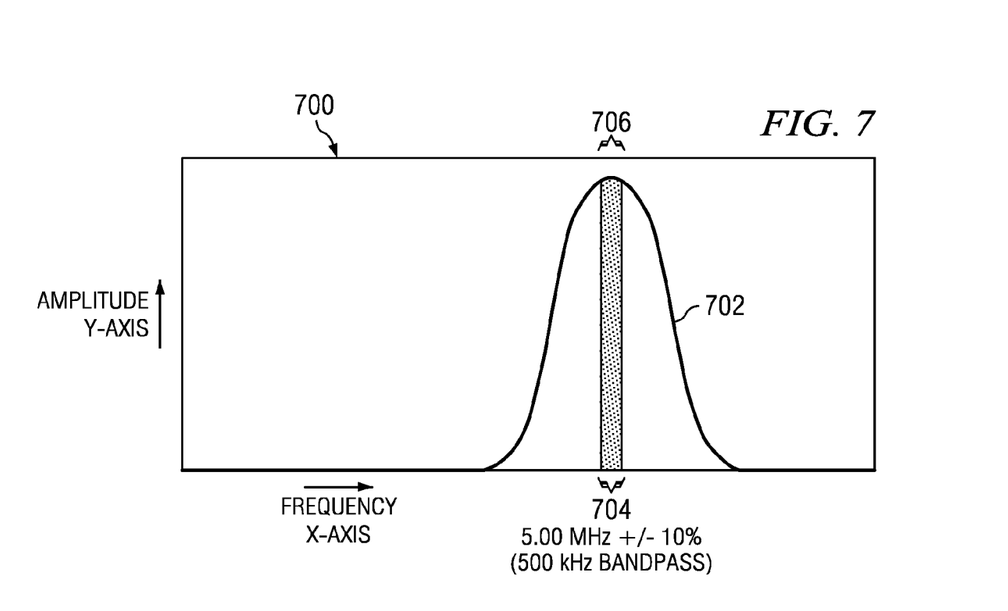
FIG. 7 is a diagram of a response provided by a bandpass filter in accordance with an advantageous embodiment.

Turning now to FIG. 7, a diagram of a response provided by a bandpass filter is depicted in accordance with an advantageous embodiment. Graph 700 illustrates a response of a filter that may be implemented as filter 310 in FIG. 3 or filter 410 in FIG. 4. In graph 700, the X-axis represents frequency and the Y-axis represents amplitude. The bandpass filter, in this example, has a center frequency, $F_0$, of 5.0 MHz. Curve 702 represents the response received by a receiving transducer, such as receiving transducer 308 in FIG. 3 or receiving transducer 408 in FIG. 4.

The frequencies in section 704 represent the center frequency of 5.0 MHz with a range of plus or minus ten percent. Thus, the range of section 704, in this example, provides a 500 kHz bandpass. Of course, the range of the bandpass may be varied using other percentages, depending on the particular implementation.

Section 706 represents the portion of curve 702 that is passed when a filter is applied to the response signal. In these examples, when the filter is placed upstream in a received transducer, the filter allows the frequency spectrum of a known and consistent character to be passed. This consistency allows for ultrasonic measurement systems having different characteristics to receive a consistent result that may be compared to a standard attenuation curve.

Figure 8:
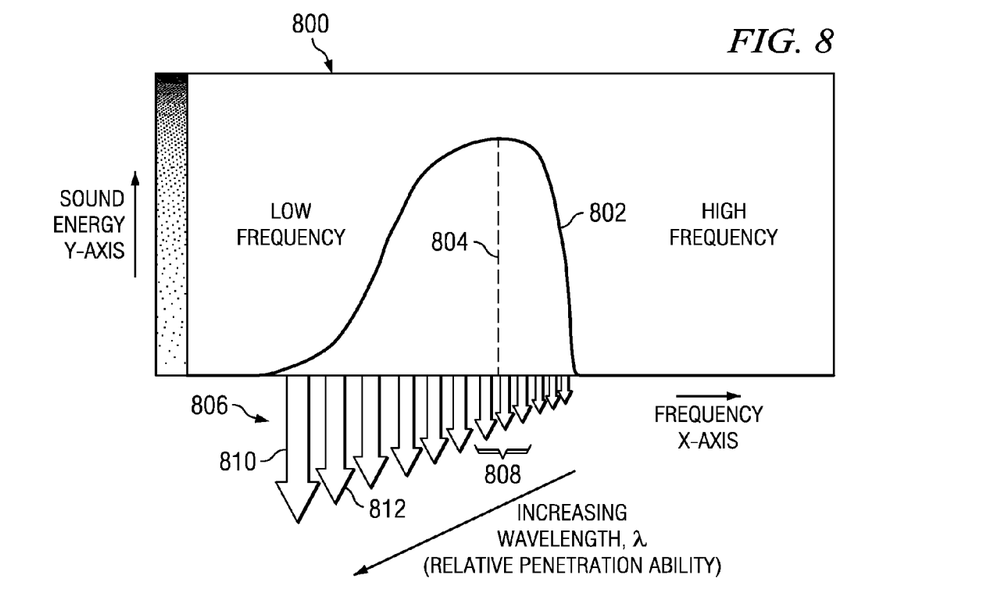
FIG. 8 is a diagram illustrating interacting effects of transmission energy and wavelength in accordance with an advantageous embodiment.

Turning now to FIG. 8, a diagram illustrating interacting effects of transmission energy and wavelengths is depicted in accordance with an advantageous embodiment. In this example, graph 800 depicts a frequency on the X-axis and sound energy on the Y-axis. Curve 802 represents the energy received by a receiving transducer over different frequencies in response to a signal being transmitted into a material. Frequency 804 is the center frequency of the transmit frequency, in these examples.

Low frequencies penetrate structures with porosity better than high frequencies. An ultrasonic frequency content is typical in most ultrasonic measurement systems. This signal is modified as the signal passes through a porous material. The center frequency of the exiting signal or response signal detected by the receiving transducer and is typically lower than the center frequency 804 of the entering signal.

As a result of this frequency filtering effect, the energy received by the receiving transducer is a function of both the frequency content of the transmitting transducer and the excitation energy transmitted by the transmitting transducer. The highest excitation energy is centered around the center transmit frequency of $f_0$. The highest energy in the received signal, however, depends on the wavelength of the sound interacting with the material. As a result, the transmission capability increases with lower frequencies, but the energy of the signal depends on the center frequency of the transmitting transducer.

In these examples, arrows 806 represents the increasing wavelength of the signal transmitted, in which relative penetration ability increases as the wavelength increases. The arrows in section 808 have the highest energy because they are arrows representing the pulse closest to the center frequency of the transmitting transducer. Arrows farther away from section 808 have less energy. Examples are arrow 810 and arrow 812, which have the highest penetrating ability, in these examples.

The different advantageous embodiments eliminate the variation caused by the bandwidth of the ultrasonic measurement system in which the transmitting transducers and the receiving transducers may have variations. These variations provide an ability to utilize a universal attenuation curve between different ultrasonic measurement devices. In these illustrative examples, a universal attenuation curve may be used by different ultrasonic measurement systems with consistent results through identifying a filter for use in the different ultrasonic measurement systems.

Through the use of a filter, such as a bandpass filter, only a selected portion of the frequency spectrum is measured or detected by the ultrasonic measurement system. With the different advantageous embodiments, any configuration for an ultrasonic measurement system or transducer combination may be used. The results, in terms of attenuation, are the same as long as sufficient energy is present to penetrate the part being tested.

In these examples, the absolute gain is measured in decibels, and the attenuation, ΔdB, also is measured in decibels. In these advantageous embodiments, the filter used does not standardize the absolute gain level needed to penetrate the material. The standardization provided in the different embodiments is used only to measure the attenuation loss in a transmitted signal caused by voids in the material. The decibel unit of measurement is derived from the following relationship:

decibels=20×log[$A_1/A_2$]

where:
dB=decibels
$A_1$=first signal amplitude
$A_2$=second signal amplitude

In the case of the absolute gain level needed to penetrate the material, the decibel level setting on the instrument is related to an increase in receiver gain over some internal reference level. In the case of the measurement of attenuation loss, the decibel value recorded by the inspector is related to the change in amplitude between a reference received signal and a new received signal.

Figure 9:
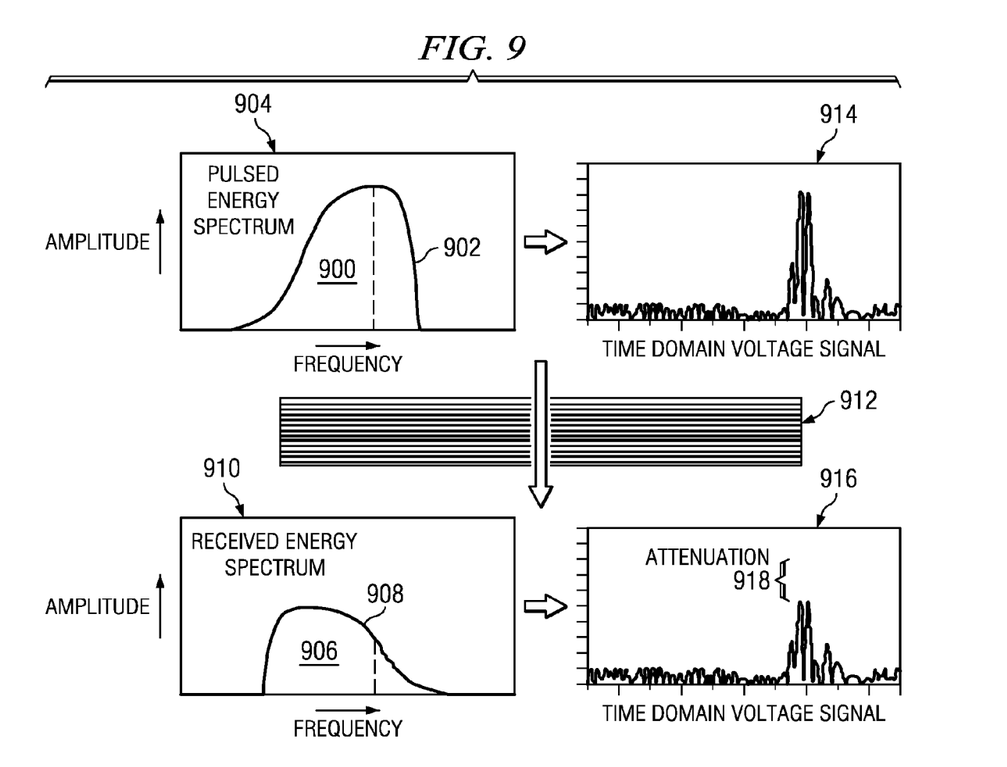
FIG. 9 is an illustration of how transmission and receive spectra are related to decibel measurements of attenuation in accordance with an illustrative embodiment.

Turning now to FIG. 9, an illustration of how transmission and receive spectra are related to decibel measurements of attenuation is depicted in accordance with an illustrative embodiment. Area 900 under transmitted spectrum curve 902 in graph 904 represents the entire energy of an ultrasonic pulse entering a composite part. Area 906 under received spectrum curve 908 in graph 910 represents the entire energy received after the pulse has passed through and has been attenuated by the same composite part 912. These energy envelopes in the frequency domain are manifested in ultrasonic instrumentation as a voltage signal in the time domain, with an amplitude corresponding to the energy level of the frequency spectrum, as shown in graphs 914 and 916. A difference in the amplitude is present between graphs 914 and 916. Section 918 shows the difference or reduction in amplitude between these graphs. Section 918 represents the attenuation that occurs from transmitting an ultrasonic pulse through composite material 912. The voltage signal is monitored for changes in amplitude with the output recorded in decibels.

Figure 10:
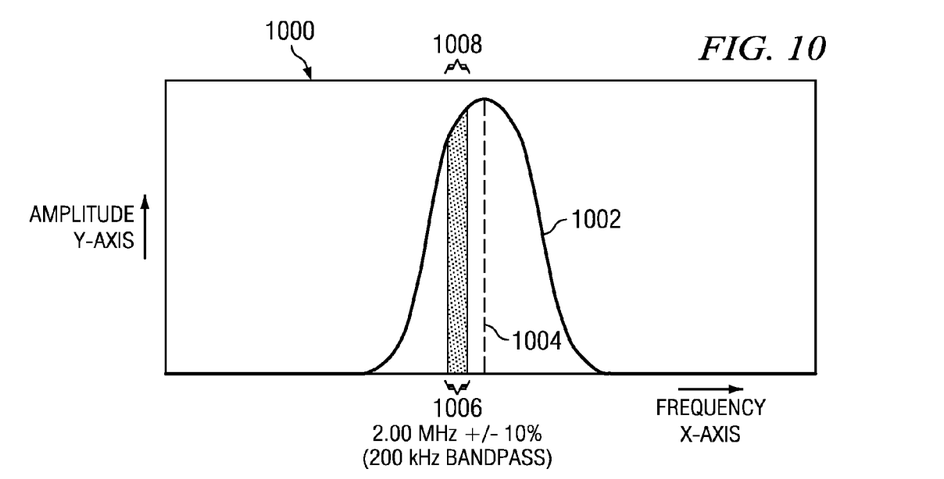
FIG. 10 is a graph of a response provided by a narrow bandwidth spectrum transducer in accordance with an advantageous embodiment.

Turning now to FIG. 10, a graph of a response provided by a narrow bandwidth spectrum transducer is depicted in accordance with an advantageous embodiment. In this example, in graph 1000, the Y-axis represents the amplitude and the X-axis represents the frequency. In this particular example, curve 1002 represents the response signal detected by a receiving transducer, such as receiving transducer 308 in FIG. 3 or receiving transducer 408 in FIG. 4. The receiving transducer has a center frequency at frequency 1004, which is around 2.25 MHz, in this example. Section 1006 represents a 2.0 MHz bandpass filter with a plus or minus ten percent range applied. Section 1008 in curve 1002 represents the filtered signal that is passed by the bandpass filter.

Figure 11:
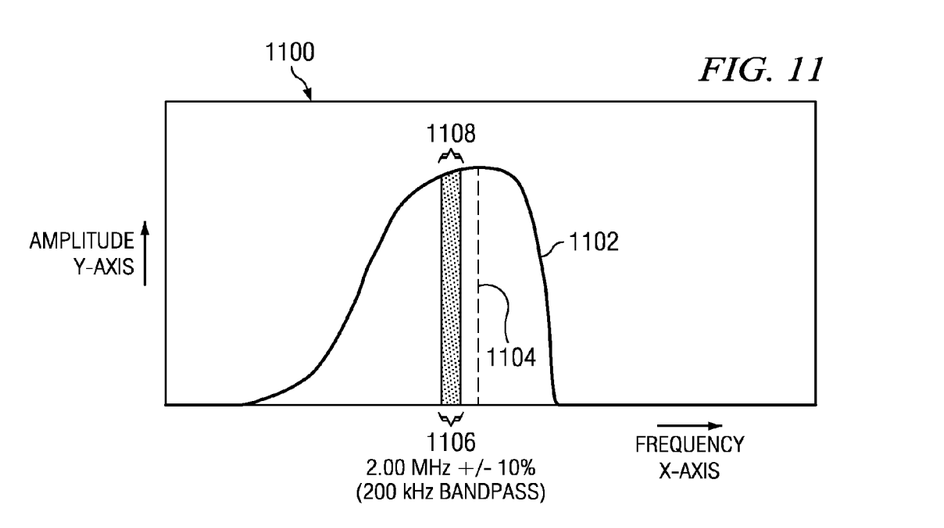
FIG. 11 is a graph of a response provided by a wide band spectrum transducer in accordance with an advantageous embodiment.

Turning now to FIG. 11, a graph of a response provided by a wide band spectrum transducer is depicted in accordance with an advantageous embodiment. In this example, in graph 1100, the Y-axis represents amplitude and the X-axis represents frequency. Curve 1102 represents a response signal that is detected by a receiving transducer, such as receiving transducer 308 in FIG. 3 or receiving transducer 408 in FIG. 4. The response signal illustrated by curve 1102 is for a "wide band" spectrum transducer.

In this example, curve 1102 has a different shape from curve 1002 in FIG. 10. This difference results in the different characteristics between the two receiving transducers. In this example, frequency 1104 represents the center frequency for this transducer and is around 2.25 MHz plus or minus ten percent. In a similar fashion, section 1106 illustrates the range of frequencies that are passed by a bandpass filter of 2.0 MHz filter. Section 1108 represents the portion of curve 1102 that is present in the modified signal after filtering occurs.

Ordinarily, curve 1102 for the wide band spectrum transducer illustrated in FIG. 11 would indicate a lower attenuation level caused by porosity. This difference is because of the increased low frequency content of the spectrum relative to the receiving transducer shown in FIG. 10. The filter compensates for the differing spectral content by discarding extraneous frequency content, and the attenuation measurement is based only on the bandpass frequencies rather than the frequencies over the entire curve.

Figure 12:
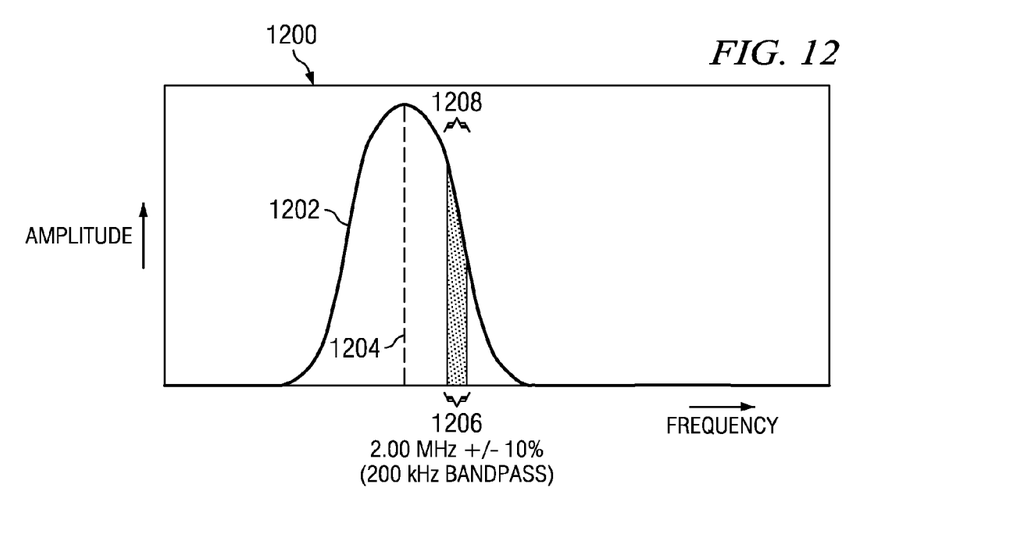
FIG. 12 is a graph illustrating a sub-optimal matching of a transducer frequency spectrum and a bandpass filter in accordance with an advantageous embodiment.

Turning now to FIG. 12, a graph illustrating a sub-optimal matching of a transducer frequency spectrum and a bandpass filter is depicted in accordance with an advantageous embodiment. In this example, graph 1200 contains curve 1202, which represents the response signal detected by a transducer. In this example, the receiving transducer has a center frequency, at frequency 1204, of around 1.0 MHz plus or minus ten percent. The bandpass filter is a 2.0 MHz filter that passes frequencies in a range shown in section 1206. The portion of the signal in curve 1202 passed by the bandpass filter is shown in section 1208. Even though sub-optimal matching occurs, the filter discards extraneous frequencies not of interest for the attenuation measurements.

Figure 13:
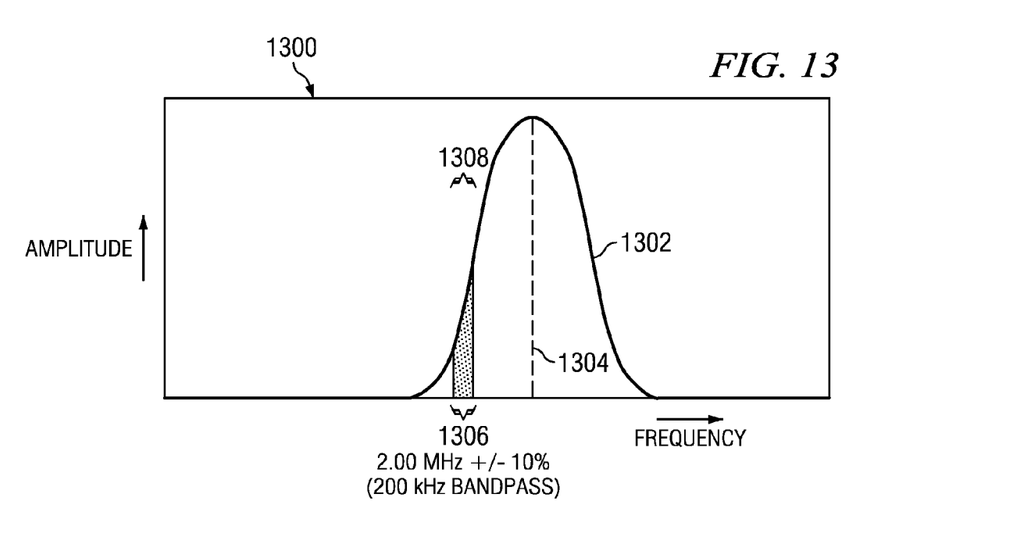
FIG. 13 is a diagram of another example of sub-optimal matching between transducer frequency spectrums and bandpass filters in accordance with an advantageous embodiment.

Turning now to FIG. 13, a diagram of another example of sub-optimal matching between transducer frequency spectrums and bandpass filters is depicted in accordance with an advantageous embodiment. In this example, graph 1300 shows a response of a signal detected by a receiving transducer in curve 1302. As depicted, frequency 1304 represents the center frequency and is around 3.5 MHz. As in the other examples, section 1306 represents the frequencies passed by a 2.00 MHz plus or minus ten percent filter. The portion of curve 1302 passed for attenuation analysis is shown in section 1308. Again, section 1208 in FIG. 12 and section 1308 in FIG. 13 are relatively small portions of the interrogating energy that passes through the filter. This portion is the area under curve 1302 in section 1308. Even though the frequencies of the transducers and the bandpass are mismatched, the different advantageous embodiments allow for a consistent attenuation measurement in the different depicted examples. In other words, the attenuation change represented by the area under curve 1302 in section 1308 (relative to measurements on a non-attenuating sample) will be consistent with the attenuation change represented by the area under the curve 1202 in section 1208 in FIG. 12 (relative to measurements on a non-attenuating sample).

Figure 14:
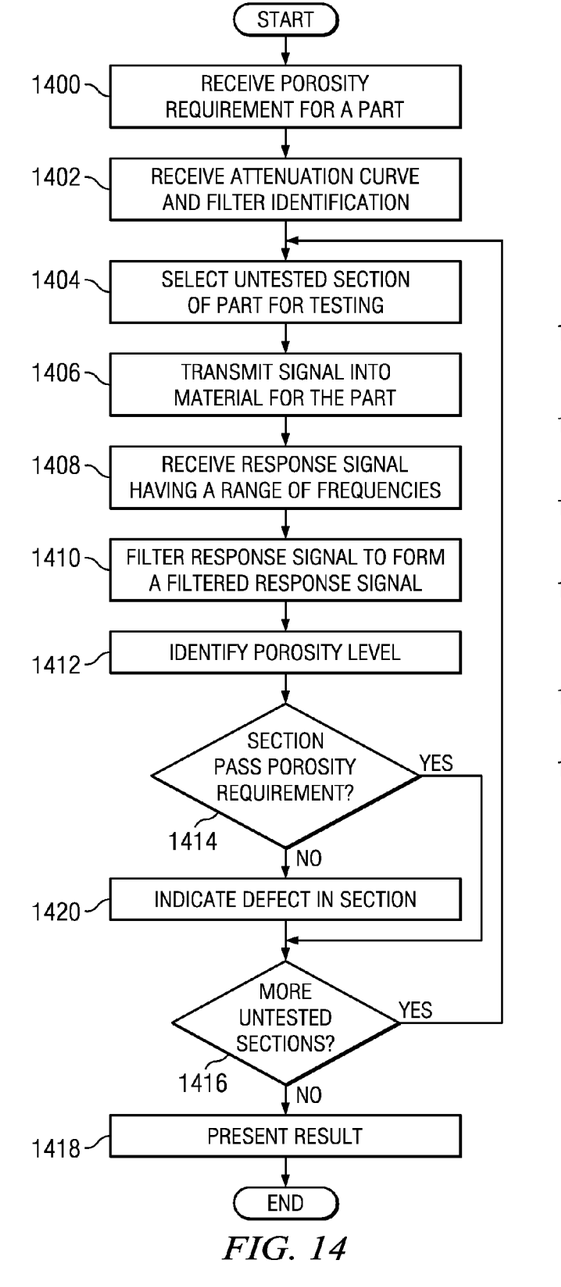
FIG. 14 is a flowchart of a process for measuring porosity levels in a part in accordance with an advantageous embodiment.

Turning now to FIG. 14, a flowchart of a process for measuring porosity levels in a part is depicted in accordance with an advantageous embodiment. The process illustrated in FIG. 14 may be implemented using an ultrasonic measurement system, such as ultrasonic measurement system 300 in FIG. 3 or ultrasonic measurement system 400 in FIG. 4. In particular, some of the steps illustrated in FIG. 14 may be implemented through a control unit implemented within data processing system, such as data processing system 600 in FIG. 6.

Depending on the particular implementation, some or all of the operations illustrated in this figure may be implemented by a user.

The process begins by receiving a porosity requirement for a part (operation 1400). Operation 1400 involves receiving a porosity level that is considered satisfactory or allowable for the particular part. This requirement is used to determine whether the porosity level measured for the material will result in the part passing or failing the requirement.

Thereafter, an attenuation curve and a filter identification are received (operation 1402). An untested section of the part is selected for testing (operation 1404). Operation 1404 selects one portion of the part for testing. Multiple sections may be selected or all of the sections in the part may be selected for testing, depending on the particular implementation. Thereafter, a signal is transmitted into the material for the part (operation 1406). Operation 1406 occurs with a transmitting transducer, such as transmitting transducer 306 in FIG. 3, emitting a signal generated by an ultrasonic pulser/receiver, such as ultrasonic pulser/receiver 304 in FIG. 3.

A response signal is received having a range of frequencies (operation 1408). Operation 1408 involves receiving the response signal through a receiving transducer, such as receiving transducer 308 in FIG. 3. The response signal is filtered to form a filtered response signal (operation 1410). A filter, such as filter 310 in FIG. 3, is used to filter the response in operation 1410, in these examples. Operation 1410 is performed using a bandpass filter in these examples. This filter may be a hardware filter or a software filter, depending on the particular implementation.

Thereafter, a porosity level is identified based on the attenuation level (operation 1412). The porosity level of the section of the part tested may be identified using a control unit, such as control unit 302 in FIG. 3. The control unit may calculate the porosity level. This calculation may be presented in a number of different ways. For example, the porosity level may be illustrated as a value or as a signal on a graph. Alternatively, the attenuation signal may be presented to a user, and the user may identify the porosity level manually.

Next, a determination is made as to whether the identified porosity level for the section passes the requirement for the part (operation 1414). Alternatively, a user may compare the results identified in operation 1414 with a graph, such as the attenuation curve in operation 1402, to determine whether the selected section passes the requirements for the part. If the section passes the porosity requirements, a determination is made as to whether additional untested sections are present (operation 1416). The control unit may perform operation 1416, in these examples. If additional untested sections are present in the part, the process returns to operation 1404 to select another section of the part for testing. Otherwise, the result of the testing is presented (operation 1418) with the process terminating thereafter.

With reference again to operation 1414, if the section does not pass the porosity requirement, an indication is made that a defect is present in the section (operation 1420). Thereafter, the process returns to operation 1416 to determine whether additional sections are present for testing.

The result presented in operation 1418 may indicate the different sections that pass the porosity test and sections that do not pass. Alternatively, if one of the sections does not pass, the process may terminate in these examples. A number of the different operations may be performed automatically if the ultrasonic measurement system is an automated one that allows for the transducers to be automatically moved from section to section over the different sections of the part being tested. Alternatively, the different operations may be performed manually, with the user identifying the different sections by moving the transducer over the different sections being tested.

Further, the process may be as simple as providing an identification of the attenuation level or presenting the signal identifying the attenuation as the transducers are moved over different sections of the part being tested.

Figure 15:
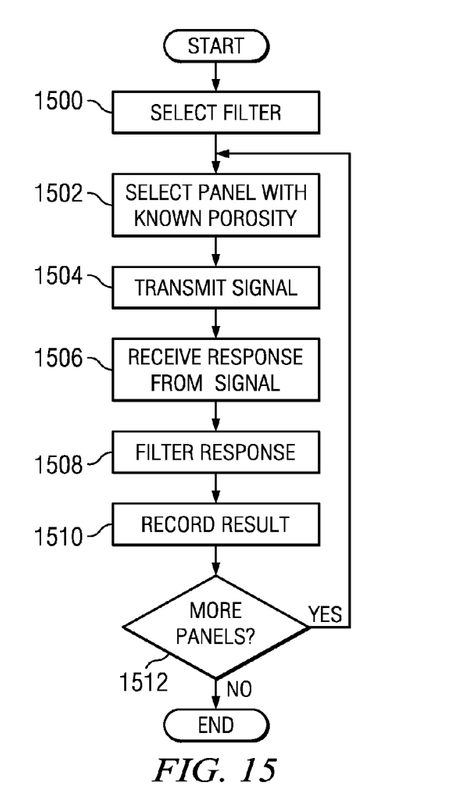
FIG. 15 is a flowchart of a process for creating an attenuation curve in accordance with an advantageous embodiment.

Turning now to FIG. 15, a flowchart of a process for creating an attenuation curve is depicted in accordance with an advantageous embodiment. The process in FIG. 15 may be implemented to provide an attenuation curve for use with ultrasonic measurement systems. The operations illustrated in FIG. 15 may be applied to each standard that is to be used in testing porosity levels. A master set of panels for a composite material may be tested to produce a universal attenuation curve. In these examples, a master set of panels may be present for each type of composite material. The composite materials may range from, for example, five plies to one hundred sixty four plies. A panel may be present for different porosity levels.

For example, one panel may be present for a porosity level of zero percent, a second panel may be present for a porosity level of around one percent to around three percent, another panel may be present for a porosity level from around three percent to around five percent, and another panel may be present for a porosity level greater than five percent. With this type of standard, data is gathered for each of these panels to generate an attenuation curve for distribution to different sites, subcontractors, or other groups that may have ultrasonic measurement systems used to test porosity levels in components or parts.

Still, with reference to FIG. 15, the process begins by selecting a filter (operation 1500). The selection of the filter varies, depending on the particular implementation. For example, if the material for which the attenuation curve is being generated is thinner than some selected thickness, a higher frequency filter may be selected, as compared to another material that has a thickness greater than a certain threshold level. With a thicker material, a lower frequency filter may be selected, as compared to the filter for a thinner material. Next, a panel with a known porosity is selected (operation 1502).

Thereafter, a signal is transmitted into the selected panel (operation 1504). A response is received from the signal (operation 1506). The response is then filtered (operation 1508). The result is then recorded (operation 1510). A determination is then made as to whether additional unprocessed panels are present to be processed (operation 1512). If additional unprocessed panels are present, the process returns to operation 1502 to select another panel with a known porosity level. Otherwise, the process terminates.

Figure 16:
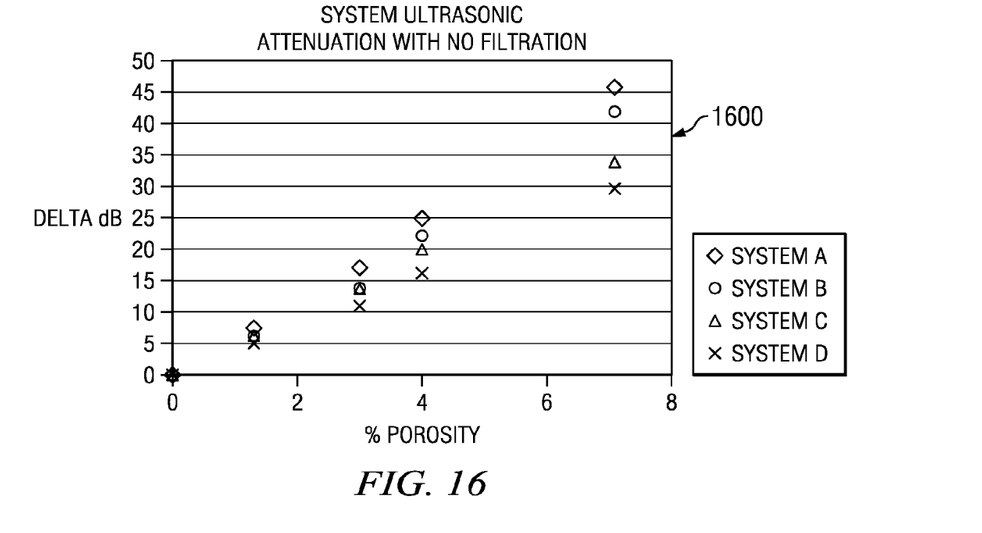
FIG. 16 is a diagram of attenuation measurements made without using a filter in accordance with an advantageous embodiment.

Turning now to FIG. 16, a diagram of attenuation measurements made without using a filter is depicted in accordance with an advantageous embodiment. Graph 1600 illustrates porosity measurements made by four different systems in which filters are not used.

Figure 17:
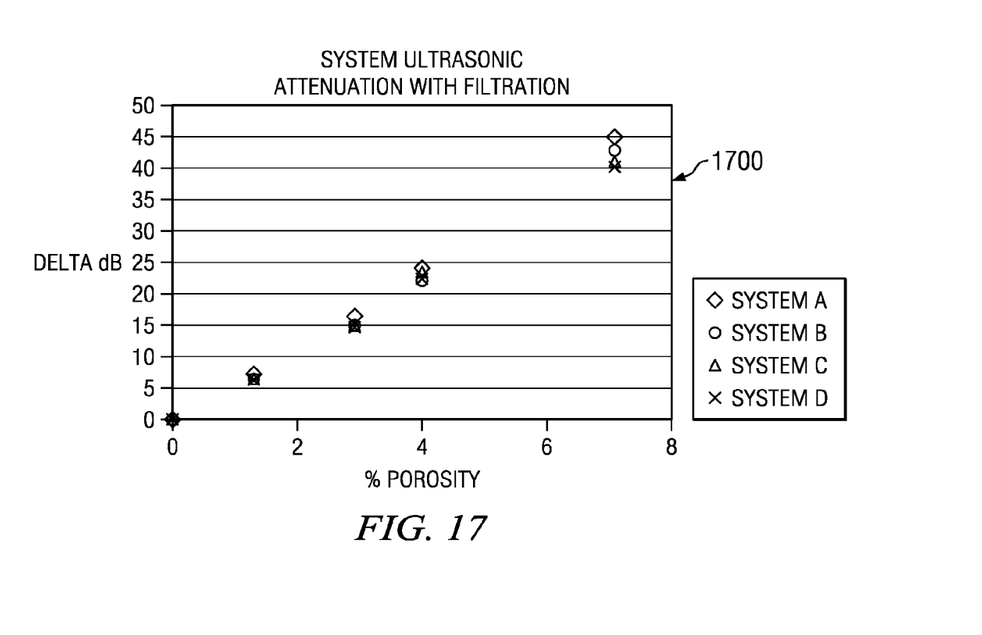
FIG. 17 is a diagram illustrating porosity measurements made with a filter in accordance with an advantageous embodiment.

Turning now to FIG. 17, a diagram illustrating porosity measurements made with a filter is depicted in accordance with an advantageous embodiment. In this example, graph 1700 shows measurements of the same part with the same four different ultrasonic measurement systems as in FIG. 16 using a bandpass filter. As can be seen, the measurements are much more consistent providing the ability to use an attenuation curve to identify porosity levels as compared to the results illustrated in FIG. 16.

Figure 18:
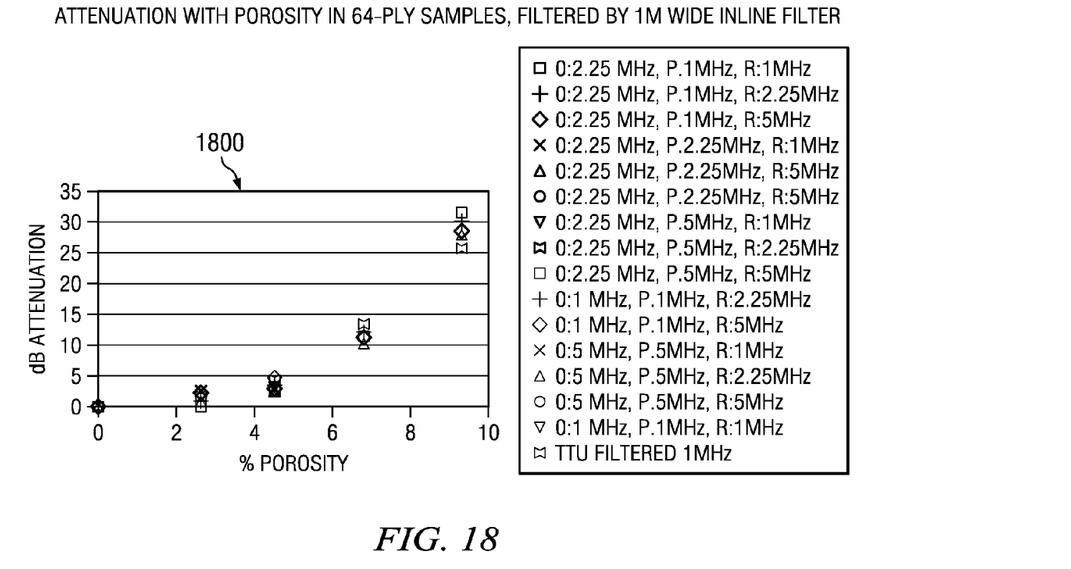
FIG. 18 is a graph illustrating attenuation data obtained using filters in an ultrasonic measurement system in accordance with an advantageous embodiment.

Turning now to FIG. 18, a graph illustrating attenuation data obtained using filters in an ultrasonic measurement system is depicted in accordance with an advantageous embodiment. In this example, graph 1800 represents attenuation with porosity in 64-ply samples. These samples were filtered using a 1.0 MHz wide inline filter. As can be seen in graph 1800, the variance between the different types of transducers in the different systems did not produce any significant deviation in results. In this example, the data point series represent measurements taken with instrument and transducers at various frequencies. The parameters were deliberately chosen to represent a sub-optimal match of system frequency with the filtering frequency. O is the instrument receiver frequency setting, P is the pulsing transducer nominal frequency, and R is the receiving transducer nominal frequency. "TTU filtered" is the control measurement using a tone burst through transmission ultrasonic system with the receiver tuned to 1 MHz and both transmit and receive transducers at 1 MHz nominal frequency. In this particular example, the filter was a 1 MHz filter with a ten percent bandwidth, noted as a "wide" inline filter since the other filter had a two percent bandwidth.

Thus, the different advantageous embodiments provide a method and apparatus for measuring porosity materials. A signal is transmitted into the material and a response is received from the transmitted signal. This received signal is filtered to pass only a selected range of frequencies. The filtered signal is compared to a reference signal to identify the porosity level of the material. In this manner, a signal filtered by the ultrasonic measurement system may be compared to a reference signal or reference data point, such as that found in an attenuation curve, to determine the porosity level of the material. The use of the filter allows for the same data to be used by different ultrasonic measurement systems, which may have different characteristics, and still obtain a consistent result.

The description of the different advantageous embodiments has been presented for purposes of illustration and description, and is not intended to be exhaustive or limited to the invention in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for measuring porosity in a composite material, the method comprising:
    identifying an attenuation curve and a filter, the attenuation curve formed from a plurality of porosity measurements made from a plurality of panels of the composite material, each of the plurality of panels having a different porosity level, and wherein the filter enables the attenuation curve to be used on a plurality of different ultrasonic measuring systems;
    emitting a first ultrasonic signal from a transmitting transducer in an ultrasonic measurement system of the plurality of different ultrasonic measuring systems into a material;
    responsive to emitting the first ultrasonic signal, receiving a second ultrasonic signal at a receiving transducer in the ultrasonic measurement system from the material;
    filtering the second ultrasonic signal to pass only frequencies in the second ultrasonic signal within a selected frequency range to form a filtered second ultrasonic signal;
    comparing the filtered second ultrasonic signal to the attenuation curve to form a comparison; and
    using the comparison to identify the porosity level of the material.

2. The method of claim 1, wherein the filtering step comprises:
    filtering the second ultrasonic signal with a filter located to pass only a portion of the second ultrasonic signal with the selected frequency range.

3. The method of claim 2, wherein the filter is a bandpass filter.

4. The method of claim 3, wherein the bandpass filter is selected from a group containing a software bandpass filter and a hardware bandpass filter.

5. The method of claim 1, wherein the filtering step comprises:
    filtering the response signal with a filter located upstream of the transmitting transducer to pass only a portion of a transmit pulse with the selected frequency range.

6. The method of claim 1, further comprising:
    reducing one or more variations in results between the different ultrasonic measuring systems by using the universal attenuation curve, wherein the one or more variations include a difference in a frequency sensitivity spectra in one more receiving transducers, a frequency content of one or more pulses, or a frequency bandwidth of one or more receiving transducers; and
    eliminating a need to provide one or more porosity calibration standards in a form of panels or sample materials;
    wherein each of the different ultrasonic measuring systems have one or more variations in the difference in frequency sensitivity spectra in one or more receiving transducers, the frequency content of one or more pulses, or the frequency bandwidth of one or more receiving transducers.

7. The method of claim 1, wherein the emitting step comprises:
    emitting the first ultrasonic signal from the transmitting transducer in the ultrasonic measurement system into a composite material.

8. A method for measuring porosity in materials, the method comprising:
    identifying an attenuation curve and a filter, the attenuation curve formed from a plurality of porosity measurements made from a plurality of panels of the composite material, each of the plurality of panels having a different porosity level, and wherein the filter enables the attenuation curve to be used on a plurality of different ultrasonic measuring systems, each of the different ultrasonic measuring systems having variations in frequency sensitivity spectra in one or more receiving transducers, a frequency content of one or more pulses, or a frequency bandwidth of one or more receiving transducers;
    transmitting a first ultrasonic signal into a material;
    responsive to transmitting the first ultrasonic signal, receiving a second ultrasonic signal originating from the first ultrasonic signal; and
    filtering the second ultrasonic signal to pass only a selected range of frequencies to form a filtered second ultrasonic signal; and
    comparing the second ultrasonic signal to the universal attenuation curve to identify the porosity level for the material.

9. The method of claim 8, wherein the filter is one of a software filter and a hardware filter.

10. The method of claim 8, wherein the filtering step comprises:
    filtering the signal transmitted into the material.

11. The method of claim 8, wherein the transmitting step comprises:
   transmitting the first ultrasonic signal into a composite material.

12. The method of claim 8, wherein the first ultrasonic signal is an ultrasound signal.

13. An apparatus comprising:
   an ultrasound signal generation unit capable of generating an ultrasound signal;
   a transmitting transducer connected to the ultrasound signal generation unit, wherein the transmitting transducer is capable of transmitting the ultrasound signal into a material;
   a receiving transducer, wherein the receiving transducer is capable of receiving a response ultrasound signal generated by the transmitting transducer transmitting the ultrasound signal into the material;
   a filter capable of filtering the response ultrasound signal received by the receiving transducer to form a modified response ultrasound signal that includes only frequencies within a selected range, wherein the filter enables an attenuation curve to be used on a plurality of different ultrasound signal generating units, each of the different ultrasound signal generating units having variations in frequency sensitivity spectra in one or more receiving transducers, a frequency content of one or more pulses, or a frequency bandwidth of one or more receiving transducers; and
   an ultrasound receiver connected to the receiving transducer, wherein the ultrasound receiver is capable of presenting the modified response ultrasound signal;
   comparing the response ultrasonic signal to the attenuation curve to identify a porosity level for the material identifying an attenuation curve and a filter, wherein the attenuation curve is formed from a plurality of porosity measurements made from a plurality of panels of the composite material, each of the plurality of panels having a different porosity level.

14. The apparatus of claim 13, wherein the filter is a hardware bandpass filter and connects the ultrasound receiver to the receiving transducer.

15. The apparatus of claim 13, wherein the filter is a software filter located in the ultrasound receiver.

16. The apparatus of claim 13, wherein the filter is connected to the transmitting transducer and filters the response signal transmitted by the transmitting transducer.

17. The apparatus of claim 13, wherein the apparatus is one of a through-transmission system and a pulse-echo system.

* * * * *